United States Patent
Li et al.

(10) Patent No.: US 9,229,015 B2
(45) Date of Patent: Jan. 5, 2016

(54) ACCURACY MANAGEMENT METHOD

(75) Inventors: Qing Li, Hitachinaka (JP); Tomonori Mimura, Kasama (JP); Shinichi Fukuzono, Hitachinaka (JP); Naomi Ishii, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1197 days.

(21) Appl. No.: 13/141,984

(22) PCT Filed: Nov. 19, 2009

(86) PCT No.: PCT/JP2009/006209
§ 371 (c)(1),
(2), (4) Date: Sep. 13, 2011

(87) PCT Pub. No.: WO2010/073479
PCT Pub. Date: Jul. 1, 2010

(65) Prior Publication Data
US 2012/0000268 A1 Jan. 5, 2012

(30) Foreign Application Priority Data
Dec. 26, 2008 (JP) ................. 2008-331830

(51) Int. Cl.
*G01N 35/00* (2006.01)
*G01D 18/00* (2006.01)
*G01N 35/02* (2006.01)

(52) U.S. Cl.
CPC .... *G01N 35/00693* (2013.01); *G01N 35/00613* (2013.01); *G01D 18/00* (2013.01); *G01N 35/00712* (2013.01); *G01N 35/025* (2013.01); *Y10T 436/10* (2015.01); *Y10T 436/11* (2015.01)

(58) Field of Classification Search
CPC .......... G01N 35/00594; G01N 35/00613; G01N 35/00693; G01N 35/00712; G01N 35/025; G01D 18/00; Y10Y 436/10; Y10Y 436/11
USPC ........ 436/8, 43, 164; 422/63, 67, 68.1, 82.05, 422/82.09; 73/1.01
See application file for complete search history.

(56) References Cited

U.S. PATENT DOCUMENTS 6,080,364 A * 6/2000 Mimura et al. ................. 422/67
7,186,217 B2 * 3/2007 Kawasaki ..................... 600/300

(Continued)

FOREIGN PATENT DOCUMENTS

| EP | 1835291 A2 | 9/2007 |
|----|------------|--------|
| JP | 04-109728 A | 4/1992 |
| JP | 11-051942 A | 2/1999 |
| JP | 2001-084034 A | 3/2001 |
| JP | 2003-057248 A | 2/2003 |

(Continued)

OTHER PUBLICATIONS

Office Action issued Oct. 1, 2012, in German Patent Application No. 11 2009 003 799.2.

*Primary Examiner* — Maureen Wallenhorst
(74) *Attorney, Agent, or Firm* — Miles & Stockbridge PC

(57) ABSTRACT

There is provided a comprehensive accuracy management method attained by including the steps of: displaying operation event information in time series in an accuracy management result chart or a calibration result chart on the same screen; accumulating a characteristic daily measurement value fluctuation pattern on the basis of a kind of an operation event; displaying the latest fluctuation pattern of measurement results and the daily measurement value fluctuation pattern in superposition with each other to warn of fluctuations which differ from the daily measurement value fluctuation pattern; and estimating and reporting the cause of the fluctuations.

17 Claims, 8 Drawing Sheets

(56) References Cited

U.S. PATENT DOCUMENTS

| | | | |
|---|---|---|---|
| 8,150,645 B2 * | 4/2012 | Kamihara et al. | 702/81 |
| 8,524,153 B2 * | 9/2013 | Mimura et al. | 422/63 |
| 8,871,080 B2 * | 10/2014 | Li et al. | 205/789 |
| 2006/0058940 A1 | 3/2006 | Kumagai et al. | |
| 2007/0217949 A1 | 9/2007 | Mimura et al. | |
| 2008/0114559 A1 | 5/2008 | Yamaguchi et al. | |

FOREIGN PATENT DOCUMENTS

| | | |
|---|---|---|
| JP | 2005-351690 A | 12/2005 |
| JP | 2006-079483 A | 3/2006 |
| JP | 2007-052629 A | 3/2007 |
| JP | 2007-248088 A | 9/2007 |
| JP | 2008-076267 A | 4/2008 |
| JP | 2008-190832 A | 8/2008 |

* cited by examiner

FIG. 4
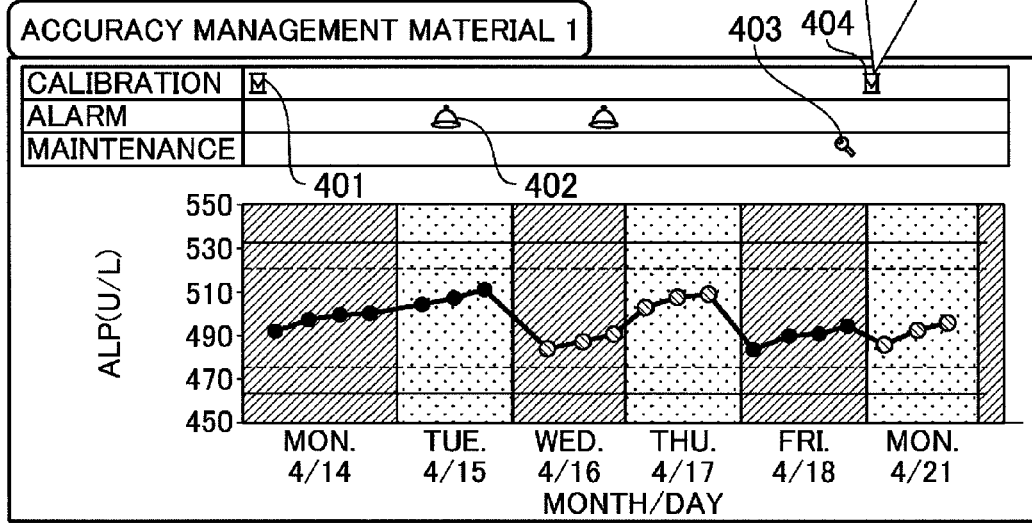
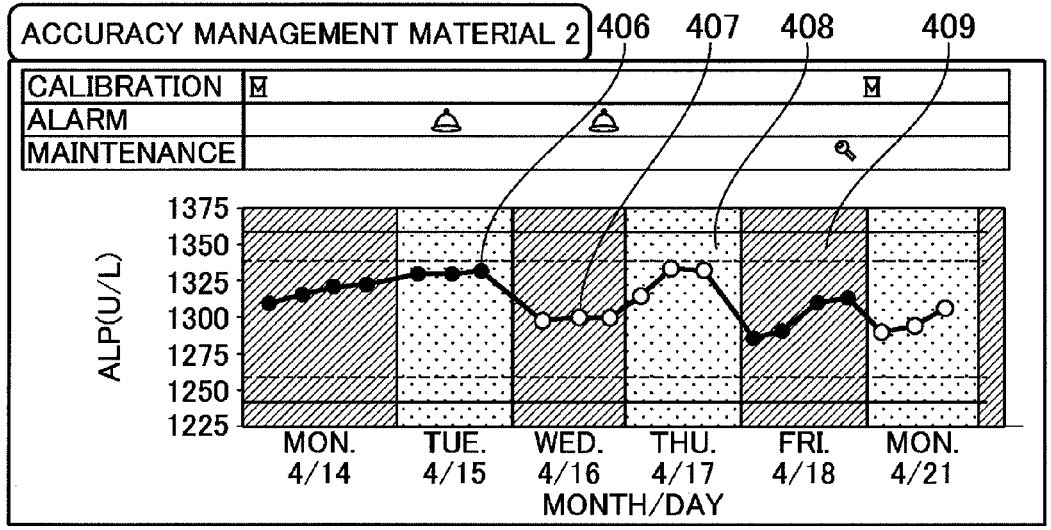
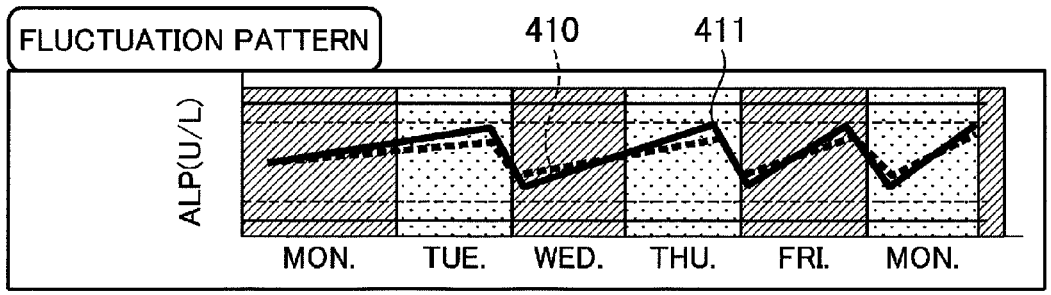

ACCURACY MANAGEMENT METHOD

TECHNICAL FIELD

The present invention relates to an accuracy management system of a clinical inspection automatic analyzer which uses patient samples primarily such as blood and urine for clinical inspection. The invention also relates to an accuracy management method which includes the steps of: concurrently displaying information about operation events of a laboratory in time series in a chart for indicating accuracy management results or calibration results; extracting a characteristic daily measurement value fluctuation pattern from fluctuation patterns of measurement results in the past for accuracy management results or calibration results to store the extracted fluctuation pattern; comparing the latest fluctuation pattern of measurement results with the daily measurement value fluctuation pattern for a period during which accuracy management is to be performed; extracting and presenting a fluctuation pattern which differs from the daily measurement value fluctuation pattern; and further analyzing the cause of the fluctuations to warn an operator of the cause of abnormal accuracy management.

BACKGROUND ART

In the accuracy management of an automatic analyzer for clinical inspection, an accuracy management material (control sample), the concentration of which is know, is interruptedly measured during intervals between measurements of patient samples, and whether or not measurement results deviate from a control value associated with the accuracy management material is checked, or circadian variation and day to day variation are checked. Thus, the precision of the automatic analyzer is assessed by the precision of the measurement results. In addition, presence or absence of abnormality in the automatic analyzer, judgment on deterioration of a reagent, preparation quality of standard solution or the like is detected by measurement results of the accuracy management material, and calibration results. These series of accuracy management are executed by a clinical laboratory technologist who summarizes the calibration results and the measurement results of the accuracy management material and records and stores the summarized data. Examples are shown as below.

At present, a plurality of accuracy management materials have already been developed, and are on the market, and management of the accuracy management materials is performed not only by clinical laboratory technologists of clinical laboratories, but also by public institutions.

(1) A clinical laboratory uses an accuracy management material sold by a reagent manufacturer on the market, inputs a concentration value and a standard deviation, which are associated with the accuracy management material, into a data management computer in a hospital as control values, and manages measurement results of the accuracy management material.

(2) A clinical laboratory uses an accuracy management material sold by a reagent manufacturer on the market, and transmits measurement result data of the accuracy management material of the clinical laboratory to the reagent manufacturer through a network line, by mail or the like. The reagent manufacturer then summarizes the data. The summarized measurement results of the accuracy management material are subjected to statistical processing, and are then sent to each hospital.

(3) An organization such as the Japan Medical Association distributes nationwide common control samples to hospitals, clinical laboratory inspection centers and the like all over the country all at once about once or twice a year to request them to perform measurement. The organization summarizes the measurement results, and then subjects the summarized measurement results to statistical processing. Besides the Japan Medical Association, the management is carried out on a prefecture basis, on a hospital group basis or the like.

(4) Manufacturers of automatic analyzers put, to practical use, systems in which automatic analyzers as own products, which have been sold and installed in clinical laboratories of hospitals and inspection centers, are connected to a service server through network lines to enable remote monitoring of the automatic analyzers.

Patent document 1 discloses the related art of the example (4). A clinical laboratory of each hospital transmits calibration results, and measurement results of an accuracy management material, which are associated with a reagent lot number, a calibrator lot number and a lot number of the accuracy management material at the time of measurement, to a support center in real time through a network line. The support center summarizes the calibration results and data of the accuracy management material, and then subjects the summarized data to statistical processing to check a change from the preceding day, and to check a deviation from a reference value. The clinical laboratory of each hospital makes an access to the support center through the network line to check a situation of the accuracy management of the automatic analyzer.

PRIOR ART LITERATURE

Patent Document

Patent document 1: JP-2007-248088-A

SUMMARY OF THE INVENTION

Problems to be Solved by the Invention

The main objects of the accuracy management systems described in the background art are to determine whether or not the measurement results of the accuracy management material fall within a control range, and to determine whether fluctuations in measurement results of the accuracy management material are systematic fluctuations or accidental ones. However, when the accuracy management is performed on the basis of the operation of laboratories, the accuracy management systems known in the prior art have problems as described below.

First, a fluctuation pattern of measurement results is not assessed on the basis of a kind of an operation event of each laboratory. In many cases, fluctuations in measurement results of an accuracy management material are considered to have been caused by an operation event such as the execution of calibration. A shape of a curve formed by accuracy management results or calibration results, which are graphed in time series, is identified as a pattern by human eyes, or the shape is identified by automatic multi-rule check or the like. In the accuracy management system, storing, as a pattern, the shape of the curve formed by the graphed accuracy management results or the graphed calibration results, and detecting an abnormal fluctuation pattern of measurement results before the measurement results go out of the control range are thought to be convenient and useful for inspection work.

However, there is no system for assessing a fluctuation pattern of measurement results on the basis of an operation event.

Second, when the cause of fluctuations in accuracy management results or in calibration results is estimated, the estimation depends on specialized knowledge and experience because related information is not sufficiently provided.

In actuality, when a fluctuation tendency is found, related screens are opened one by one, and useful pieces of information are sorted out from useless ones to organize the information, which requires much time and efforts.

Third, when the cause of fluctuations is estimated, related information may be overlooked depending on circumstances.

More specifically, in the methods known in the prior art, there are many accuracy management systems in which an alarm is issued when a measurement result exceeds a predetermined control value or a control value calculated by statistical processing of data in the past. However, when the accuracy management value goes out of a control range, objective determination of the cause of fluctuations depends on technical skill and experience, and requires much time and efforts before the estimation of the cause is achieved. To continuously provide high-quality inspection data by preventing an abnormal fluctuation tendency before an accuracy management value is exceeded, it is necessary to provide a means for keeping track of a daily measurement value fluctuation pattern for accuracy management results or calibration results, warning of an abnormal fluctuation pattern of the measurement results beforehand, and estimating and reporting the cause of the fluctuations.

Means for Solving the Problems

The abovementioned problems can be solved by the following means.

A shape of a curve based on measurement results in an accuracy management result chart or a calibration result chart is identified by an accuracy management system as a fluctuation pattern of the measurement results on an operation event basis. The accuracy management system extracts fluctuation pattern characteristics from fluctuation patterns of a plurality of measurement results in the past and stores and displays the characteristics as a daily measurement value fluctuation pattern.

Characteristic fluctuation patterns are extracted on the date and time of execution of calibration, or in the lot change timing of a reagent and in the bottle change timing of the reagent, or in the lot change timing of an accuracy management material and in the vial change timing of the accuracy management material, or in the lot change timing of a calibrator and in the vial change timing of the calibrator, or in the timing of replacement of a reactor cell, in the timing of maintenance cleaning, and the like. In addition, a drift tendency, a shift tendency or a stable tendency is extracted on a weekly basis in a manner that separates the accuracy management results or the calibration results. Moreover, a fluctuation pattern which repeats three times or more is extracted from the plurality of characteristic fluctuation patterns of the measurement results in the past on an operation event basis, and is then stored as a daily measurement value fluctuation pattern. Although the display period is weekly in a default function, the display period is not limited to weekly.

The latest fluctuation pattern is displayed in superposition with the daily measurement value fluctuation pattern to warn of a fluctuation pattern that differs from the daily measurement value fluctuation pattern.

The timing of each operation event is identified by a background color of the accuracy management chart, a style or color of a marker or an icon means. Clicking an icon of an operation event pops up a balloon window which displays information on the operation event.

Accuracy management charts or calibration result charts, which have common inspection items, are displayed on the same screen.

The cause of a fluctuation tendency in the accuracy management results or the calibration results is extracted by comparing with fluctuation tendencies of other items, and is then reported. Alternatively, the cause of the fluctuation tendency in the accuracy management results or the calibration results is extracted on the basis of a kind of an operation event and the timing thereof, and is then reported.

Effects of the Invention

Execution of the abovementioned accuracy management by hospitals or support centers provides the following effects.

The operation of laboratories is usually repeated on a weekly basis although each laboratory is operated differently from others. Therefore, fluctuation pattern characteristics are extracted and displayed from a plurality of fluctuation patterns of measurement results in the past on a weekly basis. This makes it possible to keep track of a daily measurement value fluctuation pattern on a weekly basis.

Fluctuation pattern characteristics are extracted from a plurality of fluctuation patterns of measurement results in the past, and a fluctuation pattern for the latest one week is displayed in superposition with the stored daily measurement value fluctuation pattern. This makes it possible to keep track of a fluctuation state for the latest one week.

The latest fluctuation pattern of measurement results is displayed in superposition with the daily measurement value fluctuation pattern, which makes it possible to warn of the latest fluctuation pattern of measurement results, which differs from the daily measurement value fluctuation pattern. Warning of the latest different fluctuation pattern of measurement results makes it possible to make a user aware of fluctuations in accuracy management results before a measurement result exceeds the control range of calibration results.

Displaying operation event information in time series in an accuracy management result chart or a calibration result chart on the same screen eliminates the time and efforts to open related information screens one by one, and enables the estimation of the cause of fluctuations.

Displaying, on the same screen in time series, an accuracy management chart or a calibration result chart, which shows kinds of operation events and common inspection items, facilitates the estimation of the cause of fluctuations from related information.

The cause of a fluctuation tendency in accuracy management results or calibration results is extracted and reported on an item basis on the basis of a kind of an operation event and the timing thereof, which makes it possible to facilitate the estimation of the cause.

BRIEF DESCRIPTION OF THE DRAWINGS

FIG. 4 is an ALP accuracy management chart on a two-point calibration basis;

BEST MODES FOR CARRYING OUT THE INVENTION

Figure 1:
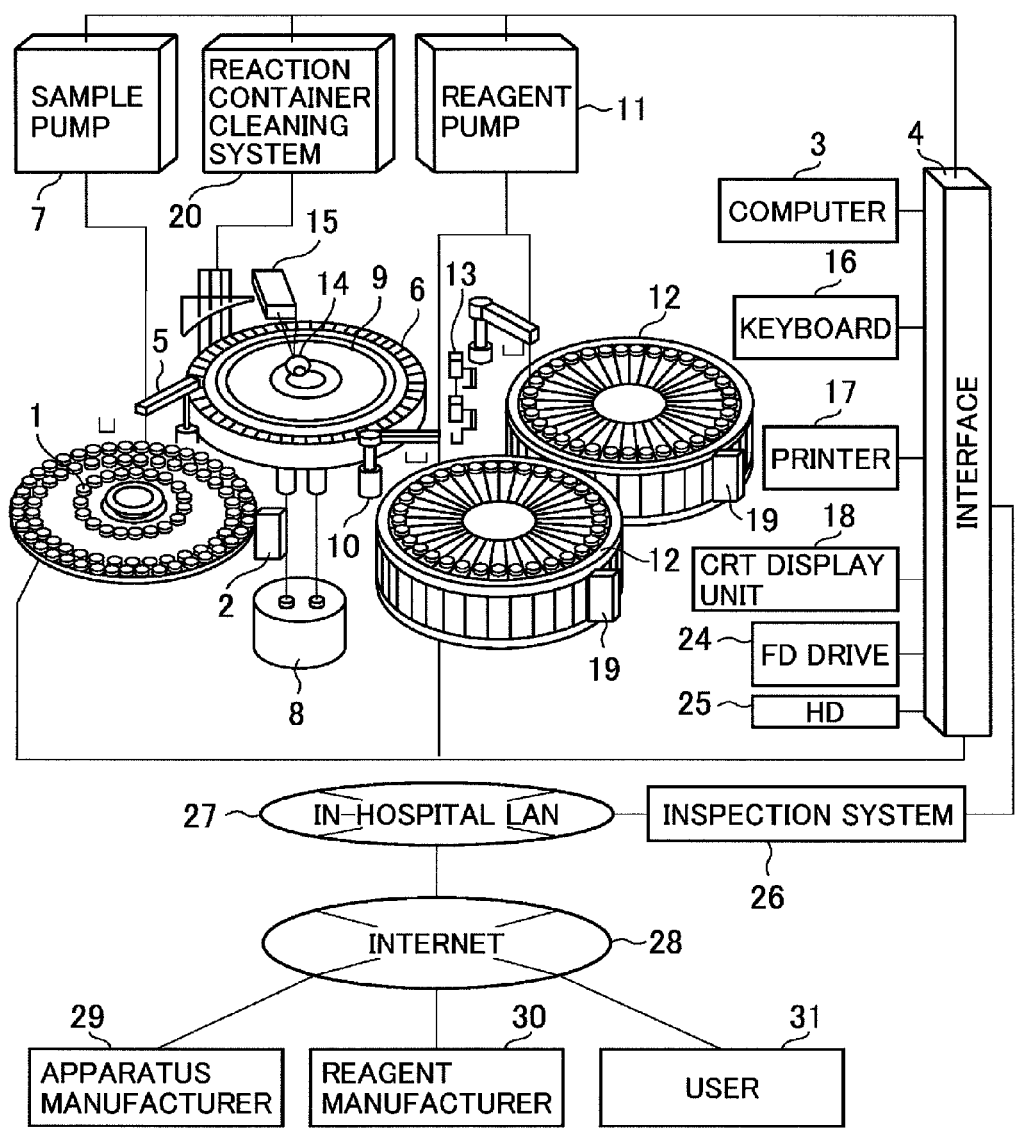
FIG. 1 is a diagram illustrating input of operation event information.

The present invention relates to an accuracy management system of a clinical inspection automatic analyzer which uses patient samples primarily such as blood and urine for clinical inspection, the accuracy management system being provided with: a means for concurrently displaying information about operation events of a laboratory in time series in a chart for indicating accuracy management results or calibration results; a means for, from a fluctuation pattern of a plurality of measurement results for a period in the past during which accuracy management has been performed, extracting characteristics of the fluctuation pattern to store the characteristics as a daily measurement value fluctuation pattern, and then displaying the characteristics; a means for warning of the latest fluctuation pattern of measurement results, which differs from the daily measurement value fluctuation pattern; and a means for extracting a cause of the fluctuations, and then reporting the cause.

First, the accuracy management of the present invention corresponds to, for example, accuracy management of the biochemical analysis and that of the immunity analysis. Accuracy management charts of the present invention correspond to, for example, an Xbar-Rs-R control chart and an Xbar-R control chart. In addition, a chart for indicating calibration results in the present invention corresponds to a graph showing S1Abs through S6Abs, K factor, reagent blank solution dominant wavelength absorbance, standard solution dominant wavelength absorbance, and a difference between twice measurements of standard solution absorbance. Moreover, a unit of a display period is one week that is the length of intervals between which the operation is repeated in a laboratory as a default function. However, the unit is not limited to one week.

A vial number of the present invention corresponds to a number for, in the same production lot, individually identifying a glass bottle container, or a plastic bottle container, which contains an accuracy management material or a calibrator. A bottle number of a reagent corresponds to a number for individually identifying a container bottle filled with the reagent in the same production lot.

Fluctuation patterns of the present invention correspond to: a shift tendency of accuracy management results, which is caused by a lot change of control; a shift tendency or a drift tendency, which is caused by a vial change of control; a shift tendency or drift tendency of calibration results, which is caused by a lot change of a calibrator; a shift tendency or drift tendency of calibration results, which is caused by a vial change of a calibrator; a shift tendency or drift tendency of accuracy management results, which is caused by a reagent lot change or a reagent bottle change; and a shift tendency or drift tendency of calibration results, which is cause by a reagent lot change or a reagent bottle change.

Operation events of the present invention correspond to changing a lot or vial of an accuracy management material, changing a reagent lot or a reagent bottle, changing a lot or vial of a calibrator, executing calibration, executing maintenance, and generating alarms. A kind of an operation event represents any of the abovementioned operation events or a combination of the operation events.

More specifically, the execution of calibration corresponds to measurement of blank calibration, span calibration, two-point calibration or multipoint calibration. The blank calibration is a calibration method in which only reagent blank absorbance is updated by use of water, physiological saline, or another blank solution containing no measuring object. The span calibration is a calibration method in which only a K value is updated by one point that is a known-concentration standard solution other than blank solutions. The two-point calibration is a calibration method in which a blank solution and one point selected from among a plurality of standard solutions are measured to update a calibration curve. The multipoint calibration is a calibration method in which a calibration curve is updated by use of all of predetermined standard solutions.

The calibration result represents absorbance or a rate of change in absorbance and calculation parameters, which are obtained by measuring a reagent blank solution or a known-concentration standard solution. The absorbance obtained here includes: absorbance obtained by measuring with a single wavelength, which is preset in an apparatus; a difference in absorbance between a dominant wavelength and a secondary wavelength, which is obtained by two wavelength measurement; or absorbance obtained by multiple-wavelength measurement. The calculation parameters are results of calculation that uses absorbance obtained by measurement, zero concentration of a reagent blank solution, and a concentration value of a known-concentration standard solution. The calculation parameters include, for example, a K value, and a difference in absorbance obtained by a dominant wavelength and a secondary wavelength.

The K value (K factor) is calculated by the following equation:

$$K=(S2-S1)/(S2Abs-S1Abs)$$

where: S2, S1 are concentration values of two calibrators respectively; and S2Abs, S1Abs are absorbance values obtained by calibration using two calibrators respectively.

The reagent blank solution absorbance is absorbance obtained by a calibrator which does not contain a measuring object (obtained by calibration that uses, for example, water or physiological saline).

The maintenance of the present invention corresponds to: cleaning or mounting of a sample dispensing probe, and clearing of the clogged sample dispensing probe; replacement or mounting of a sample dispensing pump; cleaning or mounting of a reagent dispensing probe, and clearing of the clogged reagent dispensing probe; replacement or mounting of a reagent dispensing pump; replacement of a nozzle seal; cleaning or replacement of a stirring bar; cleaning of a reaction container cleaning nozzle, and clearing of the clogged reaction container cleaning nozzle; replacement of a nozzle chip; cleaning and replacement of a reaction container; cleaning of a reaction vessel and that of a reaction vessel draining filter; replacement or mounting of a light source lamp; replacement or mounting of a pipetter seal piece; cleaning or replacement of a vacuum tank; cleaning of a washing tank; and replacement or mounting of a cooling fan. In addition, the generation of alarms is a function with which an automatic analyzer is generally provided. The alarms correspond to a data alarm of a colorimetric item, a data alarm of an electrolyte, a warning alarm, a sampling stop alarm, a stop alarm, an emergency stop alarm, and a CPU stop alarm.

A method for introducing a sample cup in the present invention corresponds to a disk-like or rack-like means.

Inspection items which are common in the present invention correspond to an inspection item for which calibration is performed by use of the same calibrator, an inspection item which uses the same stirring mechanism, or an inspection item for which measurement is performed by the same module. To be more specific, the dispensing mechanism corresponds to a sample dispensing probe, a sample dispensing pump, a reagent dispensing probe, a reagent dispensing pump and a stirring unit.

The present invention will be specifically described with reference to embodiments as below.

Embodiment 1

First, an input tool for inputting information about operation events will be described with reference to FIG. 1 as below. The bar code on a disk-like sample cup 1 is read by a sample bar code reader 2 so that information about lot and vial numbers of an accuracy management material, or about lot and vial numbers of a calibrator, is acquired to record the information in an accuracy management system for biochemical analysis. The bar code on a reagent bottle 12 is read by a reagent bar code reader 19 so that lot and bottle numbers of a reagent is acquired to record the lot and bottle numbers in an accuracy management system for automatic analysis. However, the abovementioned steps can also be performed by operator's manual input as a substitute for the use of bar codes. Maintenance information is acquired from a maintenance register of the automatic analyzer, and alarm information is acquired from the automatic analyzer, to record the maintenance information and the alarm information in the automatic analysis accuracy management system.

Alternatively, various kinds of information from the automatic analyzer are collected via Internet 28 through an in-hospital LAN 27 connected to an inspection system 26 so that the collected information can be shared among an apparatus manufacturer 29, a reagent manufacturer 30 and a user 31. Moreover, the apparatus manufacturer 29 and the reagent manufacturer 30 provide prompt action or support on the basis of the information shared with the user 31. Alternatively, the user 31 can browse and manage system information from a laboratory, such as accuracy management results and calibration results by use of the Internet 28 even from a remote site.

Figure 2:
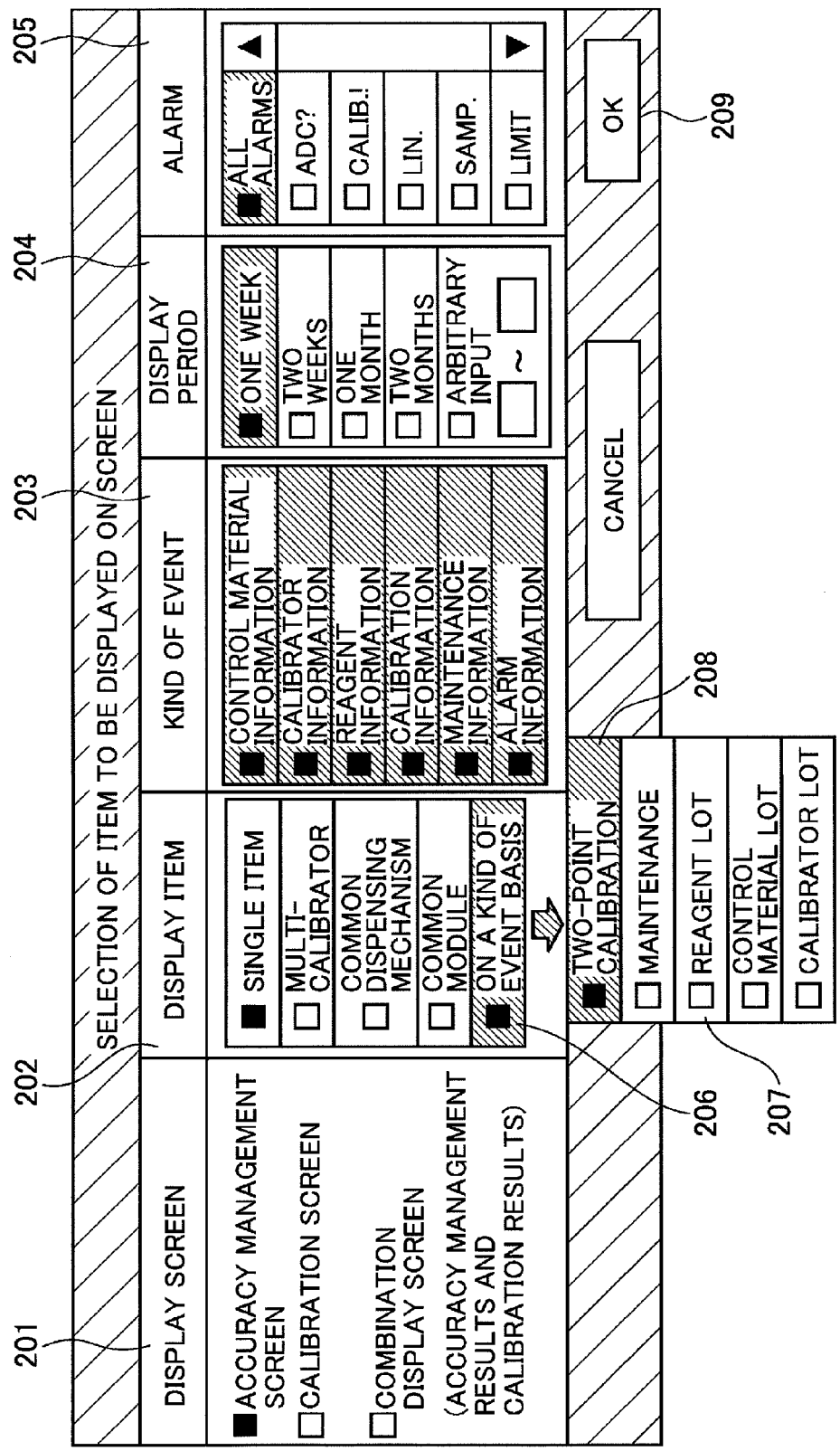
FIG. 2 illustrates a screen display selection screen.

FIG. 2 shows an example of a screen used to select items to be displayed on a screen. A selection is made from among "accuracy management screen", "calibration screen" and "combination display screen" in "Screen Name" 201, and after items are selected in "Display item" 202, "Kind of event" 203, "Display period" 204 and "Alarm" 205, clicking "OK" 209 saves the selected items. When "common calibrator", "common dispensing mechanism" or "common module, which are common factors, in the "Display item" 202 is selected and a fluctuation pattern of each item in accuracy management results or calibration results is displayed under conditions in which the common factor is used, the fluctuation tendency based on the common factor can be estimated.

For example, "one week" which is an operation period of a laboratory is set in the "Display period" 204 to display an accuracy management chart or a calibration result chart for each operation period of the laboratory.

Only alarm information which has a possibility of affecting accuracy management results or calibration results can be displayed by selecting a level and kind of alarm in the "Alarm" 205.

Selecting "on a kind of event basis" 206 in the "Display item" 202 opens a window 207, which displays accuracy management results or calibration results on a kind of event basis. For example, after "two-point calibration" 208 is selected in the window 207, clicking "OK" 209 displays accuracy management results or calibration results on a two-point calibration basis.

Embodiment 2

Figure 3:
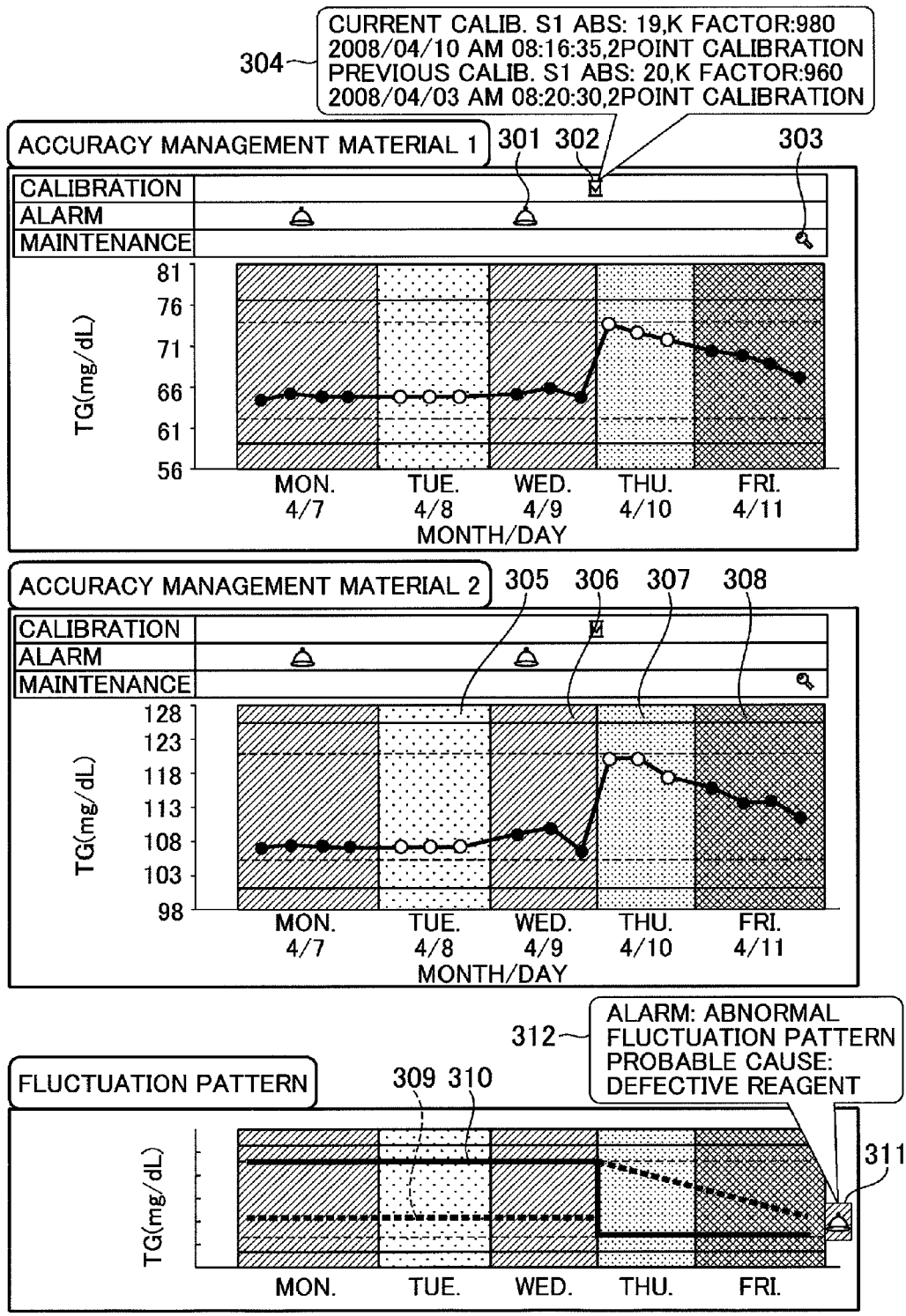
FIG. 3 is a TG accuracy management chart for one week.

Referring to FIG. 3, an accuracy management chart with a display period of one week, is shown, and a characteristic fluctuation pattern is extracted and displayed therein.

In the accuracy management chart of TG for an operation period of one week, the date and time of occurrence of an alarm 301, the date and time of execution of calibration 302 and the date and time of execution of maintenance 303 are displayed as event information in time series with icons. Clicking each event icon pops up a balloon window displaying details of a corresponding operation event. For example, clicking an icon 302 indicating two-point calibration pops up a balloon window 304 in which the date and time of occurrence of calibration, a kind of calibration and the result of calibration are displayed.

A background is divided on an operation event basis. For example, as background colors, the preceding reagent bottle is indicated with a light pink color 305, whereas the new reagent bottle is indicated with a dark pink color 306. This makes it clear at a glance that the TG reagent bottle has been changed at a boundary line at which the light pink color 305 changes to the dark pink color 306. The same lot has a background color of the same hue. The preceding reagent lot is displayed with a pink color 306, whereas the new reagent lot is displayed with a blue color 307. This makes it clearly understood that the TG reagent lot has been changed at a boundary line at which the pink color 306 of warm hue changes to the blue color 307 of cold hue. Further, it is understood that a TG reagent bottle of the new lot has been changed at a boundary line at which the blue color 307 changes to a light blue color 308 as a background color. Moreover, in general, it is rarely the case that a reagent lot which has been used once is used again after a while. Therefore, a change of a reagent lot can be briefly displayed by changing a displayed hue. A change of a bottle in the same reagent lot can be briefly displayed by changing lightness of pink with the hue kept the same.

A fluctuation pattern for the latest one week is extracted from accuracy management results of TG for the latest one week, and is then displayed. The accuracy management results of TG have a fluctuation tendency toward a higher value (higher value side shift) after the two-point calibration 302 is executed at the time of changing a reagent lot, and have a fluctuation tendency toward a lower value (lower value side drift) after the high value side shift. The fluctuation tendencies are displayed with a red line 309 as a fluctuation pattern of TG for the latest one week.

In the fluctuation pattern of TG, the timing of reagent lot change coincides with the shift timing of measurement results of a TG accuracy management material. Therefore, from TG accuracy management charts in the past, fluctuation tendencies are narrowed on a reagent lot change basis to extract fluctuation tendencies which are similar to one another three times or more, and to store the extracted fluctuation tendencies as a characteristic daily measurement value fluctuation pattern 310 indicated with a black line.

The daily measurement value fluctuation pattern 310 of TG, which is indicated with the black line, and the fluctuation pattern 309 of TG for the latest one week, which is indicated with the red line, can be superposed on each other for display.

An icon 311 indicating an alarm is displayed beside the fluctuation pattern 309 of TG for the latest one week, which differs from the daily measurement value fluctuation pattern 310. Clicking the alarm icon 311 pops up a balloon window 312 in which a kind and probable cause of the alarm are displayed. The background colors, the line colors and the balloon windows in the abovementioned example are merely given as examples, and are thus not limited to these expressions.

In the accuracy management chart of TG shown in FIG. 3, when a shift fluctuation occurs, operation event information includes only the icon of reagent lot change and the icon of two-point calibration. In the shift occurrence timing shown in the TG accuracy management chart, accuracy management results of other items have no shift fluctuation tendency, and therefore, it can be estimated that the shift fluctuation of TG has been caused by the reagent lot change.

The operation event information is displayed in time series by use of the icons 301, 302, 303 on the same accuracy management screen, which enables collection of information required to estimate a cause of the fluctuations, and enables the estimation of the cause of the fluctuations. Moreover, the work of checking whether or not other related information has been generated can be omitted.

Embodiment 3

An accuracy management chart is divided on an operation event basis. When the accuracy management chart on an operation event basis is displayed, "on a kind of event basis" 206 is selected in the "Display item" 202 shown in FIG. 2 to display the balloon window 207. For example, after the "two-point calibration" 208 is selected in the window 207, clicking "OK" 209 displays an accuracy management chart on a two-point calibration basis.

In the latest ALP accuracy management chart shown in FIG. 4, which is divided on a two-point calibration execution date basis, the date and time of execution of two-point calibration 401, 404 executed twice, the date and time of occurrence of an alarm 402, and the date and time of execution of maintenance 403, which are operation event information, are displayed in time series with icons. For example, clicking the calibration icon 404 pops up a balloon window 405 which displays results of two-point calibration executed on April 21 (Monday), the date and time of execution thereof, results of two-point calibration executed last time (April 14), and the date and time of execution thereof.

A vial number of a measured accuracy management material is displayed with a color of a marker which represents a measurement value in the ALP accuracy management chart. For example, a vial number of the preceding accuracy management material is indicated with a red circle 406, whereas a new vial number is indicated with a white circle 407. This makes it clearly understood that in the timing of change from the red circle 406 to the white circle 407, the vial of the accuracy management material has been changed.

As background colors, the preceding reagent bottle is indicated with a light pink color 408, whereas the new reagent bottle is indicated with a pink color 409. This makes it clearly understood that the ALP reagent bottle has been changed at a boundary line at which the light pink color 408 changes to the pink color 409. The background colors, the line colors and the marker colors in the abovementioned example are merely given as examples, and are thus not limited to these expressions.

Even when the background color changes from the light pink color 408 to the pink color 409, accuracy management results of ALP continuously have a drift fluctuation tendency toward the higher value side, and therefore, it can be estimated that the drift fluctuations of the accuracy management results of ALP has not been caused by the reagent bottle change. Meanwhile, the measurement results of the accuracy management material obtained from the red circle 406 or the white circle 407, each of which indicates a vial number of the same accuracy management material, have a drift fluctuation tendency toward the higher value side. In addition, when the red circle 406 changes to the white circle 407, measurement results of the accuracy management material of ALP also have a shift fluctuation tendency. Therefore, it can be estimated that the higher value side drift fluctuations and the lower value side shift fluctuations in the accuracy management results of ALP are derived from the accuracy management material. To be more specific, whether the fluctuation tendency of the accuracy management results are derived from the accuracy management material or from the reagent can be determined by comparing the changing timing of background colors from the light pink color 408 to the pink color 409 with the change timing of measurement value markers from the red circle 406 to the white circle 407.

In the latest ALP accuracy management chart that is divided on a two-point calibration execution date basis, a fluctuation pattern 410 (red line) having a drift tendency toward the higher value side is found for each vial of the accuracy management material. A daily fluctuation pattern 411 (black line) is extracted from characteristic fluctuation patterns of ALP for each vial of the accuracy management material; and the daily fluctuation pattern 411 can be displayed in superposition with the latest fluctuation pattern 410.

Embodiment 4

Figure 5:
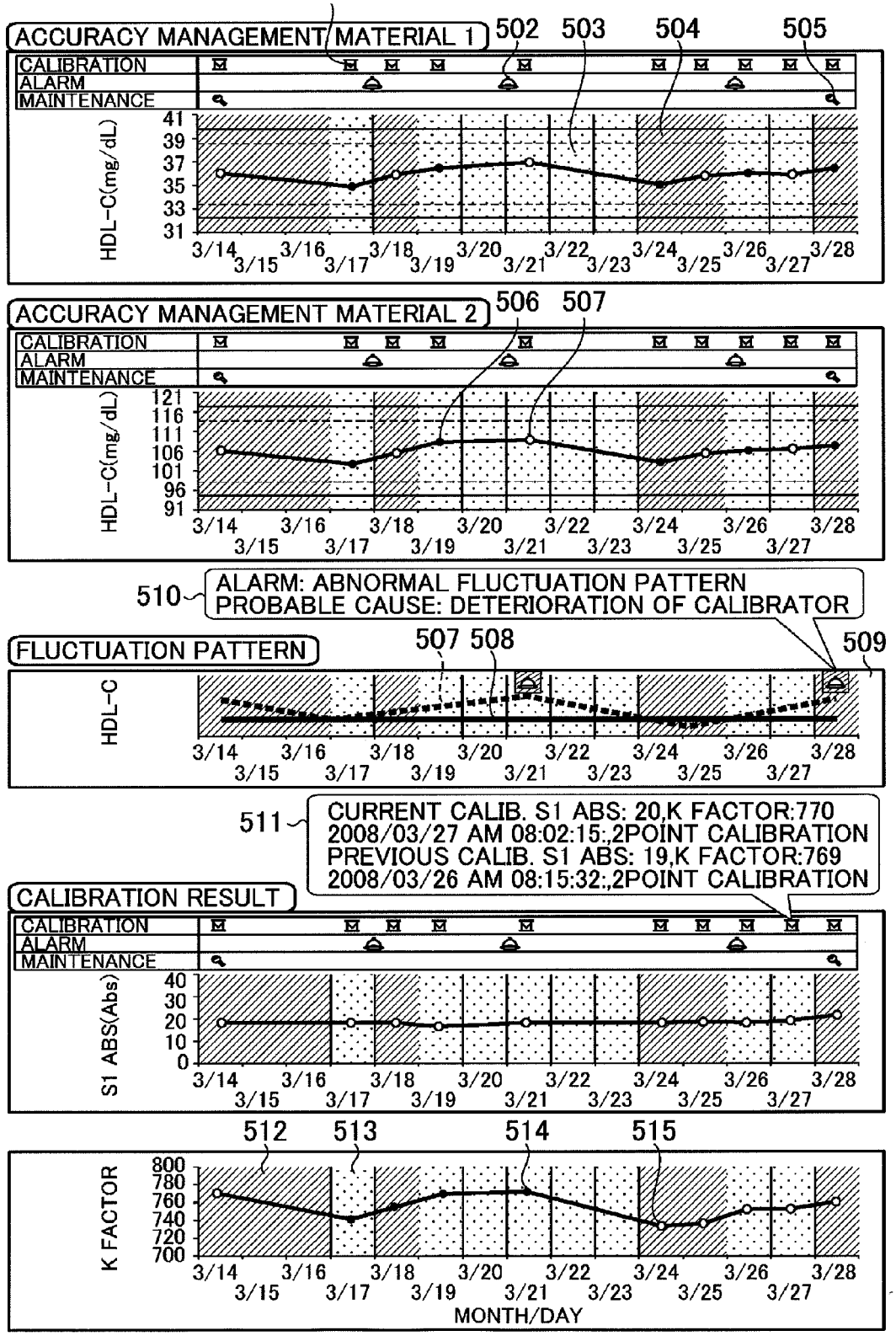
FIG. 5 illustrates a screen which concurrently displays HDL-C accuracy management charts for two weeks and a calibration result chart.

FIG. 5 shows an example in which operation event information in time series, an accuracy management chart and a calibration result chart are displayed on the same screen.

FIG. 5 illustrates a screen displayed when "combination display screen" and "two weeks" are selected in the "Display screen" 201 and the "Display period" 204 respectively on the screen shown in FIG. 2.

As shown in FIG. 5, an accuracy management chart of HDL-C for the latest two weeks and a calibration result chart are displayed on the same screen. Two-point calibration 501, the date and time of occurrence of an alarm 502 and the date and time of execution of maintenance 505, which are operation event information, are displayed in time series with icons.

In the HDL-C accuracy management chart, as background colors, the preceding reagent bottle is indicated with a light pink color 503, whereas the new reagent bottle is indicated with a pink color 504. This makes it clearly understood that the HDL-C reagent bottle has been changed at a boundary line at which the light pink color 503 changes to the pink color 504.

A vial number of a measured accuracy management material is displayed with a color of a marker which indicates a measurement value in the HDL-C accuracy management chart. For example, a vial number of the preceding accuracy management material is indicated with a red circle 506, whereas a new vial number is indicated with a white circle 507. This makes it clearly understood that in the timing of change from the red circle 506 to the white circle 507, the vial of the accuracy management material has been changed.

In the accuracy management chart of HDL-C for the latest two weeks, a fluctuation pattern 507 (red line) having a drift tendency, which does not coincide with the vial change timing of the accuracy management material and the bottle change timing of the reagent, is found. A characteristic daily measurement value fluctuation pattern 508 (black line) is extracted from the past accuracy management results of HDL-C; and the daily measurement value fluctuation pattern 508 can be displayed in superposition with the latest fluctuation pattern 507.

An alarm 509 is displayed because a fluctuation pattern 507 which differs from the daily measurement value fluctuation pattern 508 has been detected. Clicking the alarm icon pops up a balloon window 510 in which a kind and probable cause of the alarm are displayed.

In the HDL-C calibration result chart displayed on the same screen, operation event information is displayed in time series. For example, clicking an icon of the two-point calibration executed every day pops up a balloon window 511 which displays the date and time of execution, a kind and results of both the latest calibration and the preceding calibration.

In the HDL-C calibration result chart, as background colors, the preceding reagent bottle is indicated with a pink color 512, whereas the new reagent bottle is indicated with a light pink color 513. This makes it clearly understood that the reagent bottle used for calibration measurement has been changed at a boundary line at which the pink color 512 changes to the light pink color 513.

In a HDL-C calibration K factor result chart, a vial number of a calibrator is indicated with a color of a marker which represents a measurement value. For example, a blue circle 514 indicates a vial number of the preceding calibrator, whereas a white circle 515 indicates a vial number of the new calibrator. This makes it clearly understood that in the timing of change from the blue circle 514 to the white circle 515, the vial of the calibrator has been changed. The background colors, the line colors, and the shapes and colors of markers in the abovementioned example are merely given as examples, and are thus not limited to these expressions.

In the HDL-C accuracy management chart, higher value side drift fluctuations are found during the period from 3/17 to 3/21 and the period from 3/24 to 3/28; and lower value side shift fluctuations are found during the period from 3/14 to 3/17 and the period from 3/21 to 3/24. Even when the vial of the accuracy management material and the reagent bottle are changed, the drift of the HDL-C accuracy management results continues. Therefore, it can be estimated that the fluctuations of the HDL-C accuracy management results are not derived from the accuracy management material and the reagent.

In the calibration K factor result chart, the higher value side drift fluctuations are found during the period from 3/17 to 3/21 and the period from 3/24 to 3/28, and the lower value side shift fluctuations are also found during the period from 3/14 to 3/17 and the period from 3/21 to 3/24. Thus, this fluctuation pattern coincides with the fluctuation pattern 507 obtained from the accuracy management results. Therefore, it can be estimated that the fluctuation tendency in the HDL-C accuracy management result chart is derived from the calibration results.

In the calibration K factor result chart, the higher value side drift fluctuations are found during the period from 3/17 to 3/21 (blue circle 514) and the period from 3/24 to 3/28 (white circle), and the lower value side shift fluctuations are found during the period from 3/14 (white circle) to 3/17 (blue circle) and the period from 3/21 (blue circle) to 3/24 (white circle). Therefore, it can be estimated that the K factor drift fluctuations have been caused by the deterioration of the calibrator as a result of using the calibrator for five days after the calibrator was unpacked on Monday. Thus, it could be estimated that the fluctuations in the accuracy management results of HDL-C have been caused by the deterioration of the HDL-C calibrator.

Embodiment 5

Figure 6:
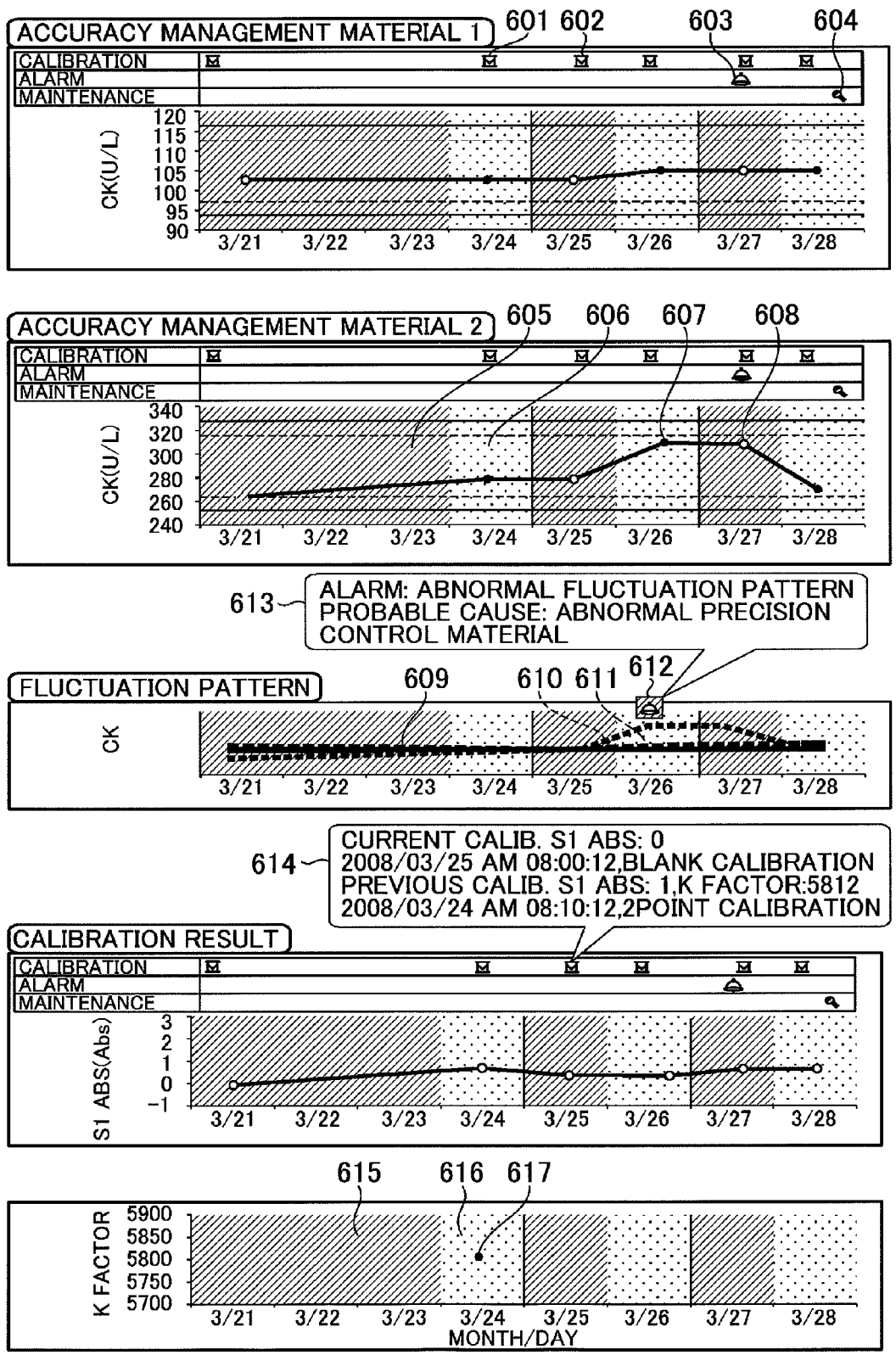
FIG. 6 illustrates a screen which concurrently displays CK accuracy management charts for one week and a calibration result chart.

Similar to FIG. 5, FIG. 6 shows an example in which an accuracy management chart of CK for the latest one week and a calibration result chart are displayed on the same screen. Two-point calibration 601, blank calibration 602, the date and time of occurrence of an alarm 603 and the date and time of execution of maintenance 604, which are operation event information, are displayed in time series with icons.

In the CK accuracy management chart, as background colors, the preceding reagent bottle is indicated with a pink color 605, whereas the new reagent bottle is indicated with a light pink color 606. This makes it clearly understood that the CK reagent bottle has been changed at a boundary line in which the pink color 605 changes to the light pink 606.

A vial number of an accuracy management material is indicated with a color of a marker which represents a measurement value. For example, as markers, a vial number of the preceding accuracy management material is indicated with a red circle 607, whereas a vial number of the new accuracy management material is indicated with a white circle 608. This makes it clearly understood that in the timing of change from the red circle 607 to the white circle 608, the vial of the accuracy management material has been changed.

A fluctuation pattern in the accuracy management chart of CK for the latest one week is not related to the vial change timing of the control material and the bottle change timing of the reagent, and thus a fluctuation pattern 609 of a low-density level indicated with a blue line differs from a fluctuation pattern 610 of a high-density level indicated with a red line. For this reason, it can be estimated that the fluctuation tendency in the accuracy management result of CK is not derived from the reagent, but derived from the accuracy management material.

A characteristic daily fluctuation pattern 611 (black line) is extracted from the past accuracy management results of CK; and the daily fluctuation pattern 611 can be displayed in superposition with the latest fluctuation patterns 609, 610. The fluctuation pattern 609 of the low-density level control material of CK indicated with the blue line coincides with the accuracy management results in the past. However, the fluctuation pattern 610 of the high-density level control material of CK indicated with the red line differs from the daily measurement value fluctuation pattern, and therefore an alarm 612 is displayed. Clicking the alarm icon 612 pops up a balloon window 613 in which a kind and probable cause of the alarm are displayed.

In the CK calibration result chart displayed on the same screen, operation event information is displayed in time series. For example, clicking a blank calibration icon pops up a balloon window 614 which displays the date and time of execution, a kind and results of both the latest calibration and the last calibration. The background colors, the line colors, the balloon windows, and the color and shape of the markers in the abovementioned example are merely given as examples, and are thus not limited to these expressions.

Embodiment 6

Figure 7:
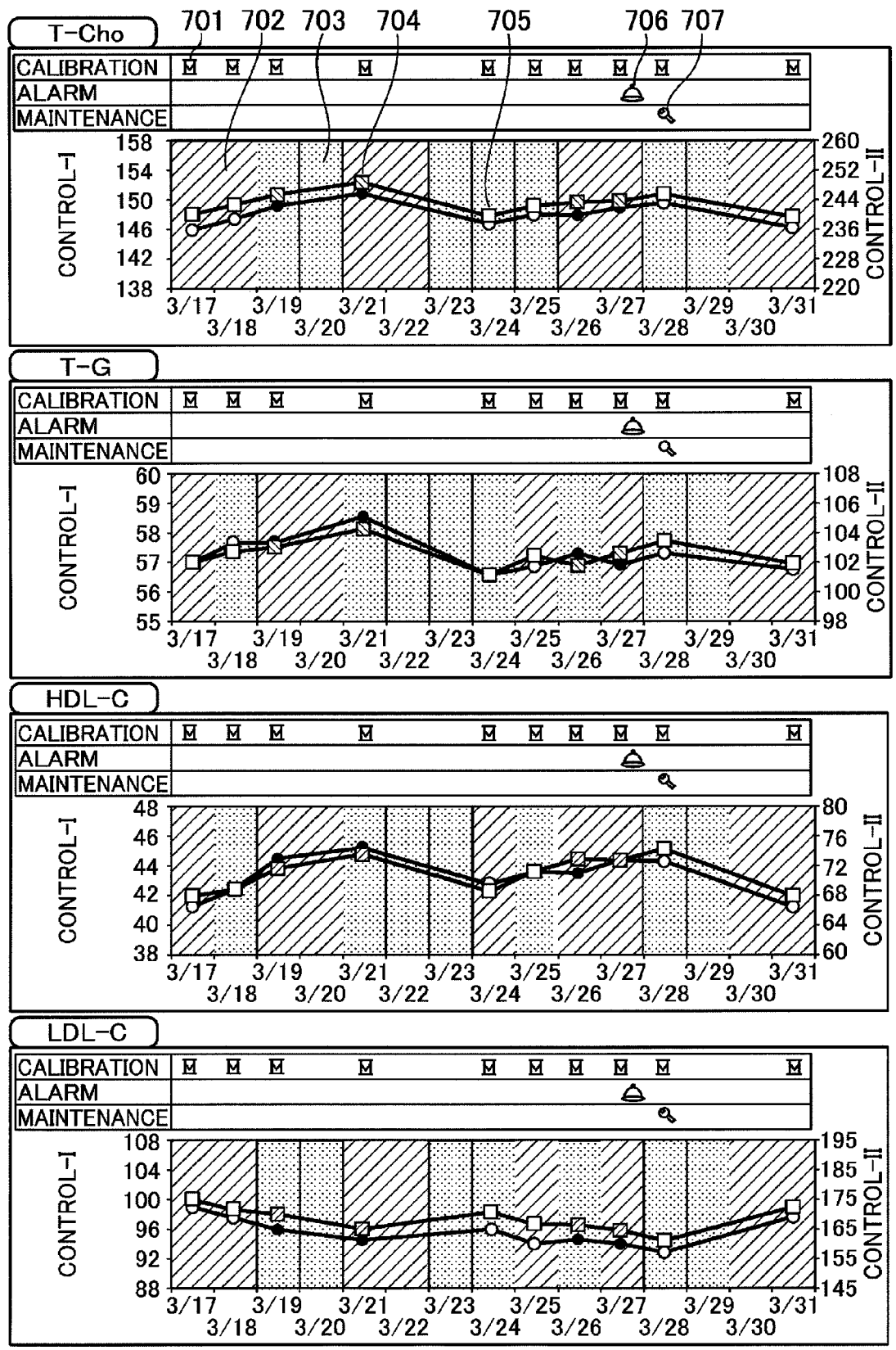
FIG. 7 is an accuracy management chart illustrating four items of lipid for which a common calibrator is used.
Figure 8:
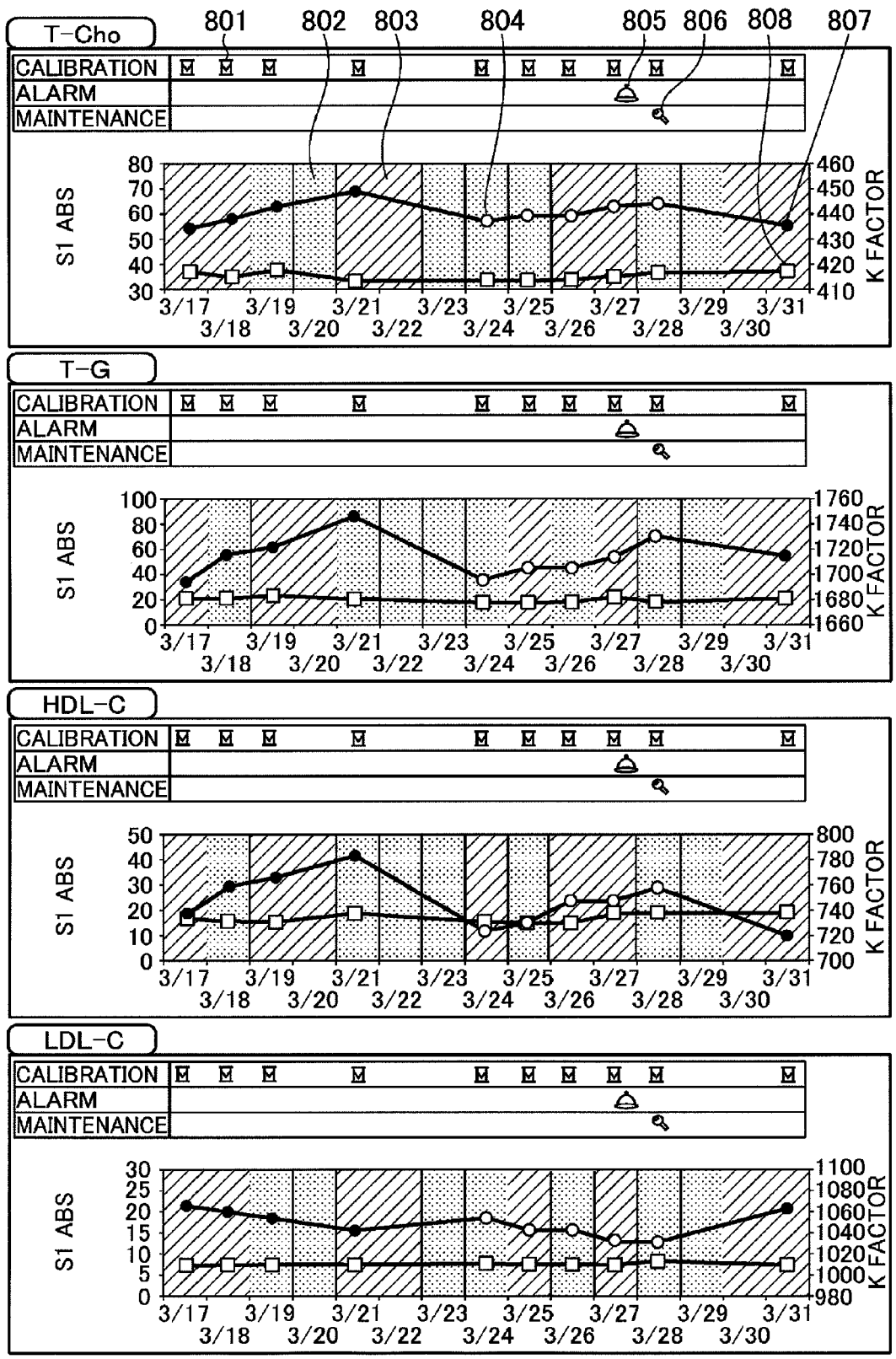
FIG. 8 is a calibration result chart illustrating four items of lipid for which a common calibrator is used.

FIGS. 7 and 8 show examples in which a plurality of inspection items measured by using the same calibrator, which is generally called a multi-calibrator, are displayed on the same screen. FIG. 7 illustrates measurement values of respective items; and FIG. 8 illustrates S1Abs and K factors of respective items.

FIGS. 7 and 8 illustrate screens displayed when "multi-calibrator" and "two weeks" are selected in the "Display item" 202 and the "Display period" 204 respectively on the screen shown in FIG. 2.

FIG. 7 is an accuracy management chart illustrating four items of lipid (T-Cho, TG, HDL-C and LDL-C) for which a common calibrator is used. The date and time of execution of calibration 701, the date and time of occurrence of an alarm 706 and the date and time of execution of maintenance 707 are displayed as operation event information. As background colors, the preceding reagent bottle is indicated with a blue color 702, whereas the new reagent bottle is indicated with a light blue color 703. This makes it clearly understood that the reagent bottle has been changed at a boundary line at which the blue color 702 changes to the light blue color 703.

A kind of an accuracy management material is displayed with a shape of a marker which represents a measurement value; and a vial number of the accuracy management material is displayed with a color of the marker. For example, a control 1 is displayed with a circle marker, and a control 2 is displayed with a square marker. Vial numbers of the preceding accuracy management materials are displayed with filled markers (filled red circle, filled blue square) 704 respectively; and vial numbers of the new accuracy management materials are displayed with void markers (void circle, void square) 705 respectively. This makes it clearly understood that in the timing of change from the filled markers 704 to the void markers 705, the vials of the accuracy management materials have been changed respectively.

In the accuracy management chart illustrating four items of lipid (T-Cho, TG, HDL-C and LDL-C), drift fluctuations are found during the period from 3/17 to 3/21 and the period from 3/24 to 3/28, and shift fluctuations are found during the period from 3/21 to 3/24 and the period from 3/28 to 3/31. However, with respect to the drift fluctuations during the period from 3/17 to 3/21 and the period from 3/24 to 3/28, the reagent bottle of each item has been independently changed, and therefore, it can be estimated that the drift fluctuations are not caused by the change of the reagent bottles. Moreover, even when the vial of the accuracy management material is changed, the drift fluctuation tendency continues. Therefore, it can be estimated that the drift fluctuations are not caused by the deterioration of the accuracy management material.

FIG. 8 is a calibration result chart illustrating four items of lipid (T-Cho, TG, HDL-C and LDL-C) for which a common calibrator is used. The date and time of execution of calibration 801, the date and time of occurrence of an alarm 805 and the date and time of execution of maintenance 806 are displayed as operation event information. As background colors, the preceding reagent bottle is indicated with a light blue color 802, whereas the new reagent bottle is indicated with a blue color 803. This makes it clearly understood that the reagent bottle has been changed at a boundary at which the light blue color 802 changes to the blue color 803.

A kind of a calibration result is indicated with a shape of a marker which represents a measurement value of the calibration result. For example, S1Abs is displayed with a square marker; and a K factor is displayed with a circle marker. Moreover, a vial number of a calibrator is indicated with a color of a marker. For example, a vial number of the preceding calibrator is displayed with a white circle 804, whereas a vial number of the new calibrator is displayed with a red circle 807. This makes it clearly understood that in the timing of change from the white circle 804 to the red circle 807, the vial of the calibrator has been changed. The background colors, the line colors, and the shapes and colors of markers in the abovementioned example are merely given as examples, and are thus not limited to these expressions.

In the calibration result chart illustrating four items of lipid (T-Cho, TG, HDL-C and LDL-C) for which a common calibrator is used, S1Abs is stable. However, a drift fluctuation tendency is found in the K factor during the period from 3/17 to 3/21 and the period from 3/24 to 3/28; and a shift fluctuation tendency is found in the K factor during the period from 3/21 to 3/24 and the period from 3/28 to 3/31. With respect to the drift fluctuations during the period from 3/17 to 3/21 and the period from 3/24 to 3/28, the same vial of the calibrator is used. The shift fluctuations of the K factor during the period from 3/21 to 3/24 and the period from 3/28 to 3/31 is found when the vial of the calibrator is changed. Therefore, it can be estimated that the fluctuations found in four items of lipid are caused by the deterioration of the calibrator after the vial is opened.

DESCRIPTION OF REFERENCE NUMERALS

1 Cup of sample
2 Sample bar code reader
3 Computer
4 Interface
5 Sample dispensing probe
6 Reaction container
7 Sample pump
8 Thermostatic bath
9 Reaction disk
10 Reagent dispensing probe
11 Reagent pump
12 Reagent bottle
13 Stirring unit
14 Light source
15 Multi-wavelength photometer
16 Keyboard
17 Printer
18 CRT display unit
19 Reagent bar code reader
20 Reaction container cleaning system
24 FD drive
25 HD
26 Inspection system
27 In-hospital LAN
28 Internet
29 Apparatus manufacturer
30 Reagent manufacturer
31 User

The invention claimed is:

1. An accuracy management method comprising:
a measurement step for repetitively measuring a sample at specified intervals;
a measurement result storing step for storing a plurality of measurement results measured in the measurement step;
a fluctuation pattern extraction step for extracting a fluctuation pattern for at least one inspection item based on a change with time in the measurement results stored in the storing step and an operation event including at least one of changing a lot or vial of an accuracy management material, changing a lot or bottle of a reagent, changing a lot or vial of a calibrator, executing calibration, executing maintenance, or generating an alarm; and
a fluctuation pattern storing step for storing the fluctuation patterns extracted in the fluctuation pattern extraction step.

2. The accuracy management method of claim 1, wherein the sample is at least either an accuracy management sample or a calibrator.

3. The accuracy management method of claim 2, wherein the accuracy management sample has a known measurement value associated with at least one inspection item.

4. The accuracy management method of claim 1, wherein the sample includes concentration calibrator solutions, the measurement results measured in the measurement step include a concentration of at least one inspection item, a K factor, an absorbance of each concentration calibrator solution, and a dominant wavelength absorbance of each concentration calibrator solution, the K factor is calculated according to the following equation:

$$K=(S2-S1)/(S2Abs-S1Abs),$$

S2 and S1 are concentration values of the calibrators, and S2Abs, S1Abs are absorbance values obtained by calibration using the calibrators.

5. The accuracy management method of claim 1, wherein the fluctuation pattern is determined based on at least one of a shift tendency, a drift tendency and a stable tendency of the measurement results measured in the measurement step.

6. The accuracy management method of claim 1, further comprising
a display step for displaying fluctuation patterns for each inspection item for an optionally set period based on the operation event.

7. The accuracy management method of claim 6, further comprising
a display step for displaying information about the operation events concurrently together with measurement results in time series.

8. The accuracy management method of claim 6, further comprising
a display step for concurrently displaying the operation events together with measurement results of a common inspection item in time series, the common inspection item being an inspection item for which:
calibration is performed by a same calibrator,
dispensing is performed by a same dispensing mechanism,
measurement is performed by a same measurement module, or
measurement is performed by a same analysis cell.

9. The accuracy management method of claim 6, further comprising
a fluctuation cause extraction step for extracting a cause of a fluctuation tendency found in accuracy management results or calibration results based on the operation event.

10. The accuracy management method of claim 9, further comprising
an output step for outputting the fluctuation cause extracted in the fluctuation cause extraction step.

11. The accuracy management method of claim 6, further comprising
an identification step for identifying a timing of an operation event by displaying at least one of a background color, a style of a marker, a color of the marker, or an icon on an accuracy management chart.

12. The accuracy management method of claim 11, further comprising
a display step for, in response to receiving a selection of the icon by a user, displaying detailed information about an operation event.

13. The accuracy management method of claim 11, further comprising
a display step for, when an icon representing a date and time of execution of calibration is clicked, displaying the result of the calibration, and current and previous values of the date and time of execution.

14. The accuracy management method of claim 1, further comprising
a superimposing step for displaying a latest fluctuation pattern of the measurement results and the fluctuation pattern stored in the fluctuation pattern storing step in superposition with each other.

15. The accuracy management method of claim 14, further comprising
a determination step for determining whether or not a deviation of the fluctuation pattern of the measurement results from the stored fluctuation pattern is a predetermined value or more.

16. The accuracy management method of claim 15, further comprising
a notification step for, when a result of the determination step determines that the deviation is the predetermined value or more, notifying of the result of the determination.

17. The accuracy management method of claim 1, wherein the inspection item includes T-Cho, TG, ALP, CK, HDL-C or LDL-C.

* * * * *